United States Patent
Laghi (10) Patent No.: US 6,991,444 B1
(45) Date of Patent: Jan. 31, 2006

(54) APPARATUS FOR CASTING A PROSTHETIC SOCKET UNDER VACUUM

(76) Inventor: Aldo A. Laghi, 14410 Eagle Point Dr., Clearwater, FL (US) 33762

(*) Notice: Subject to any disclaimer, the term of this patent is extended or adjusted under 35 U.S.C. 154(b) by 504 days.

(21) Appl. No.: 10/065,547

(22) Filed: Oct. 29, 2002

(51) Int. Cl.
*A61F 2/60* (2006.01)
*A61F 2/76* (2006.01)

(52) U.S. Cl. .................. 425/2; 264/223; 264/DIG. 30; 425/389; 623/901

(58) Field of Classification Search .............. 425/2, 425/388, 389, 405.1; 264/222, 223, DIG. 30; 623/901
See application file for complete search history.

(56) References Cited

U.S. PATENT DOCUMENTS

| | | | | |
|---|---|---|---|---|
| 1,351,789 A | * | 9/1920 | Rowley | 264/222 |
| 2,488,922 A | * | 11/1949 | Mead | 264/DIG. 30 |
| 3,995,002 A | * | 11/1976 | Brown | 264/223 |
| 4,307,056 A | * | 12/1981 | Meyer | 264/222 |
| 5,258,036 A | * | 11/1993 | Edenbaum et al. | 264/DIG. 30 |
| 5,376,132 A | * | 12/1994 | Caspers | 623/901 |
| 5,503,543 A | * | 4/1996 | Laghi | 425/2 |
| 5,879,605 A | * | 3/1999 | David | 425/2 |
| 5,885,509 A | * | 3/1999 | Kristinsson | 425/2 |
| 5,971,729 A | * | 10/1999 | Kristinsson et al. | 425/2 |
| 5,980,576 A | * | 11/1999 | Graf et al. | 264/222 |

FOREIGN PATENT DOCUMENTS

| | | | |
|---|---|---|---|
| ES | 2032705 A6 | * | 2/1993 |
| ES | 2036499 A6 | * | 5/1993 |
| GB | 2116432 A | * | 9/1983 |
| GB | 2149309 A | * | 6/1985 |

* cited by examiner

*Primary Examiner*—Robert B. Davis
(74) *Attorney, Agent, or Firm*—Ronald E. Smith; Smith & Hopen, P.A.

(57) ABSTRACT

A prosthetic socket is made by wrapping water-soaked plaster bandages around a residual limb or around a prosthetic liner within which is disposed a residual limb, and positioning a vacuum wick in overlying relation to the plaster bandages. The residual limb, prosthetic liner, plaster bandages, and vacuum wick means are then inserted into a vacuum bladder. The vacuum bladder is sealed and a predetermined vacuum is applied internally to the bladder until the plaster hardens into a negative cast. The residual limb is manipulated through the vacuum bladder to modify the geometry of the plaster before the plaster hardens. The negative cast is removed from the residual limb and a positive cast is produced by pouring plaster into the negative cast. A thermoplastic sheet is thermoformed over the positive cast or a carbon-epoxy matrix is laminated over the positive cast. This eliminates reduction and modification of a hard positive cast.

17 Claims, 6 Drawing Sheets

APPARATUS FOR CASTING A PROSTHETIC SOCKET UNDER VACUUM

BACKGROUND OF INVENTION

1. Field of the Invention

This invention relates, generally, to the art of prosthetics. More particularly, it relates to a method and apparatus for casting a prosthetic socket under vacuum.

2. Description of the Prior Art

The making of a prosthetic socket begins with a prosthetist taking a negative cast of an amputee's stump, also known as a residual limb. Filling the negative with plaster then makes a positive.

The positive is then reduced by a factor depending upon the physiology of the residual limb so that the prosthetic socket will fit properly thereon. Typically, the amount of reduction is 3% to 10%, depending upon the maturity of the residual limb, the amount of redundant tissue, the gender of the patient, the vascular history of the patient, and other such considerations. Layers of plaster are removed by hand using blades and scraping tools until the desired reduction is achieved. The layer removed should be as uniform as possible.

U.S. Pat. No. 5,503,543 discloses a pressure-casting machine used in the industry to provide a more uniform reduction. The machine displaces fluid from a residual limb by applying a uniform pressure thereto between 80–300 mm Hg for a predetermined amount of time. Sufficient fluid is displaced from the residual limb to ensure that the negative cast made from the casting will be of the desired size.

One drawback of pressure type casting machines is that manipulation of the residual limb during the hardening of the cast cannot be performed when such a machine is used. Another drawback arises from the fact that when pressure is applied to the bladder, the machine pushes itself away from the residual limb. This phenomenon occurs because the proximal end of the residual limb lacks an equivalent section of pressurized bladder to match the force exerted by the pressure in the bladder at the distal end of the residual limb. The force pushing the bladder away from the patient must equal the force applied by the amputee onto the pressure bladder. However, the force exerted by the amputee is not perfectly controllable. Accordingly, variations occur in the casting process, resulting in variations in the dimensions of the negative cast.

In performing the steps of the above-described casting process, the prosthetist puts a prosthetic liner on a residual limb and then wraps a plastic separator known as a cling wrap over the liner. If a liner is not used, the cling wrap is applied directly to the residual limb. Plaster bandages that have been soaked in water are then wrapped around the residual limb.

As an alternative to such plaster bandages, a urethane-impregnated fabric that has been soaked in water may be used in place of the plaster bandages. The urethane reacts with the water and turns the fabric into a rigid structure. Urethane-impregnated fabrics have been used for years by prosthetists in the making of immobilization casts.

In the description and claims that follow, terms such as "plaster means" or "plaster bandage means" should be understood as including urethane-impregnated fabric as well.

The steps then change depending upon whether the job is to be completed by hand or by machine.

If the job is to be completed by hand, the prosthetist manipulates the plaster by hand to provide the modifications to the geometry of the plaster as deemed appropriate for the physiology of the residual limb. Significantly, this hand manipulation of the plaster is performed while the plaster is hardening.

After the plaster has hardened, the negative cast is cut longitudinally and removed from the residual limb. Pouring plaster into the negative then produces a positive.

When the positive has hardened, blades and scraping tools are used to manually reduce the circumference of the positive as uniformly as possible along its length, section by section. Although the reduction process is laborious, it retains the geometry of the modifications imparted at the time of casting.

A properly fitting prosthetic socket is produced from the modified cast by thermoforming a thermoplastic sheet over the positive cast or by laminating a carbon-epoxy matrix over the positive cast.

If the job is to be completed by machine, the prosthetist wraps the plaster in cling wrap, places the wrapped stump in a pressure-casting bladder and applies adequate pressure for a predetermined amount of time. This causes the plaster to harden into a negative cast. The negative cast is then cut longitudinally and removed from the residual limb. Pouring plaster into the negative cast then produces a positive.

When the positive has hardened, the prosthetist makes the necessary modifications according to the physiology of the residual limb by adding plaster where needed or by carving our sections of the positive cast. The modifications must be made on the hardened positive cast because the pressure bladder prevents manipulation of the residual limb while the plaster is hardening.

A properly fitting prosthetic socket is made from the modified cast by thermoforming a thermoplastic sheet over the positive cast or by laminating a carbon-epoxy matrix over the positive cast.

A prosthetic casting machine is therefore needed that would allow manipulation of the plaster means while the negative cast is hardening.

Moreover, there is a need for a positive casting machine that would allow the application of positive pressure on the negative cast while the plaster means is hardening.

However, in view of the prior art considered as a whole at the time the present invention was made, it was not obvious to those of ordinary skill in the pertinent art how the identified needs could be fulfilled.

SUMMARY OF INVENTION

The long-standing but heretofore unfulfilled need for an improved apparatus and method of making a prosthetic socket is now met by a new, useful, and nonobvious invention.

In a first embodiment, a prosthetic liner is positioned in overlying relation to a residual limb and a first plastic separator is placed into overlying relation to the liner. Plaster bandage means that have been soaked in water are wrapped around the first plastic separator. A second plastic separator is applied in overlying relation to the plaster bandage means and a vacuum wick means is positioned in overlying relation to the second plastic separator. The residual limb, liner, first plastic separator, plaster bandage means, second plastic separator, and said vacuum wick are inserted into a vacuum bladder. A hemostatic latch is then sealed over a proximal end of the vacuum bladder and a predetermined vacuum is applied internally to the vacuum bladder for a predetermined amount of time until the plaster means hardens into a negative cast. The residual limb is manipulated through the vacuum bladder before the plaster means hardens to modify the geometry of the plaster means as appropriate for the physiology of the residual limb. The negative cast is removed from the residual limb and a positive cast is produced by pouring plaster into the negative cast. A finished prosthetic socket is then made by thermoforming a thermoplastic sheet over the positive cast or by laminating a carbon-epoxy matrix over said positive cast.

In a second embodiment, a liner is not used. Accordingly, the first plastic separator is applied directly to the residual limb. In all other respects, the second embodiment follows the teachings of the first embodiment.

An important object of this invention is to eliminate reduction and modification of a hard positive cast.

A closely related object is to provide means allowing a prosthetist to perform manipulation of plaster means while a negative cast is hardening.

A more general object is to advance the art of prosthetics by reducing the difficulty inherent in manufacturing a prosthetic socket.

Another general object is to increase the comfort of amputees by providing a method and apparatus for making a prosthetic socket that more closely conforms to the particular physiology of the user.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

Figure 1:
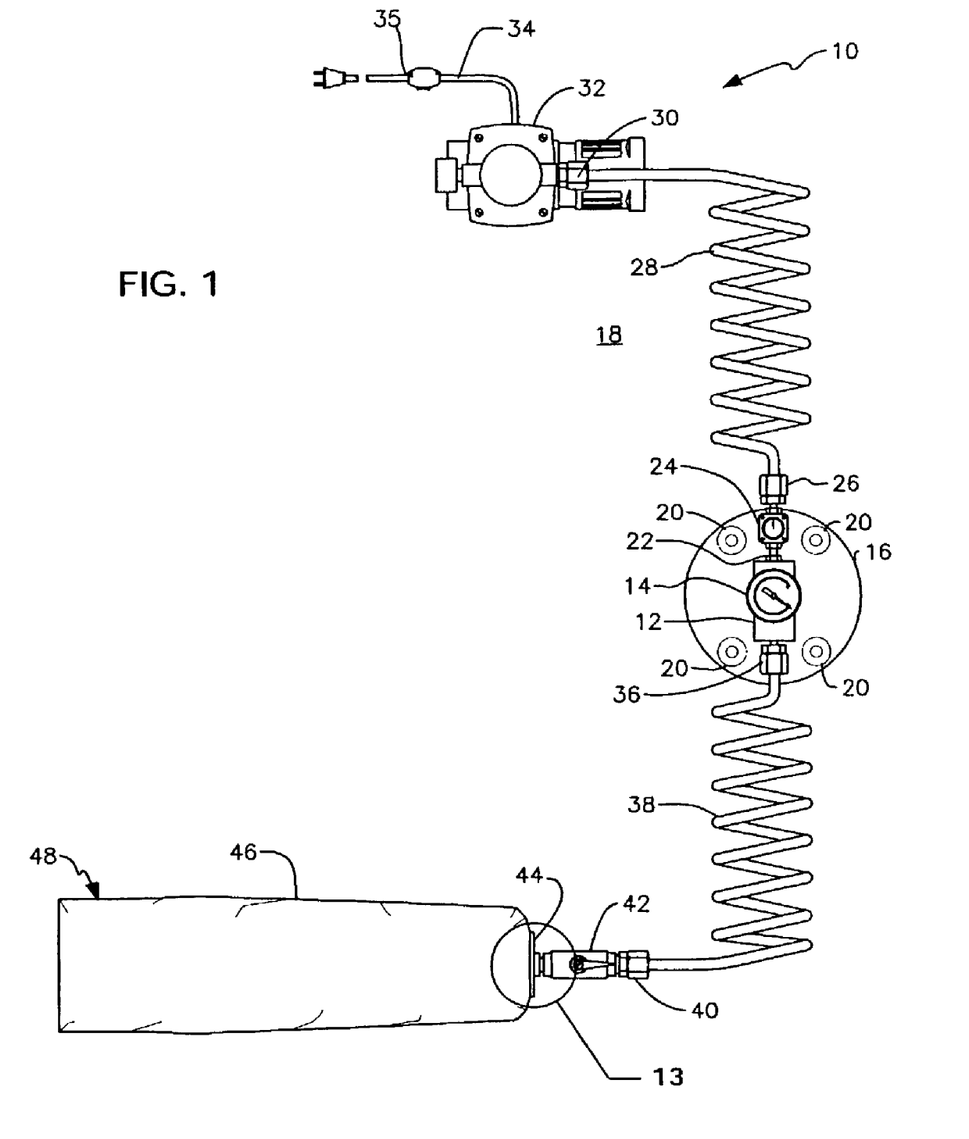
FIG. 1 is a top plan view of the novel apparatus in its assembled configuration.

Referring to FIG. 1, it will there be seen that the reference numeral 10 denotes an illustrative embodiment of an apparatus that performs the steps of the novel method.

Apparatus 10 includes vacuum gauge 14 that surmounts manifold 12. A plurality of fasteners, not shown, mount manifold 14 to clear acrylic disc 16.

Disk 16 is secured to a suitable support surface such as a work bench table top 18 by a plurality of headless suction cups, collectively denoted 20.

Manifold 12 is connected to vacuum source 32 by an assembly that includes reducing nipple 22, vacuum regulator 24, and first tube fitting 26 for interconnecting vacuum regulator 24 and first polyurethane coiled tubing 28. Second tube fitting 30 interconnects tubing 28 with said vacuum source 32. Power cord 34, including switch actuator 35, connects vacuum pump 32 to a suitable power source such as 115 volts rms.

The vacuum is transmitted from manifold 12 to third tube fitting 36 that provides fluid communication between manifold 12 and second polyurethane coiled tubing 38. Fourth tube fitting 40 interconnects tubing 38 and ball valve 42. Reference numeral 44 indicates the vacuum bladder connector assembly that engages vacuum bladder 46 and which communicates the vacuum to the interior of said bladder.

Figure 2:
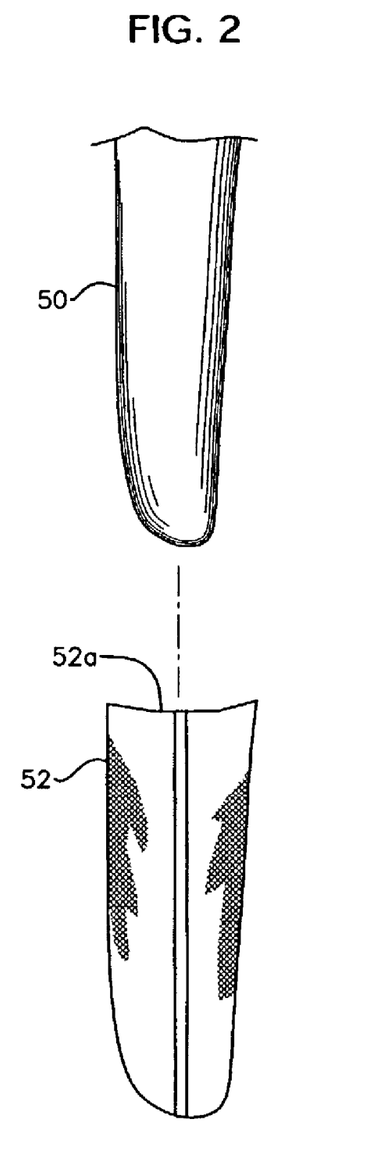
FIG. 2 is an exploded view depicting the insertion of a residual limb into a liner.
Figure 3:
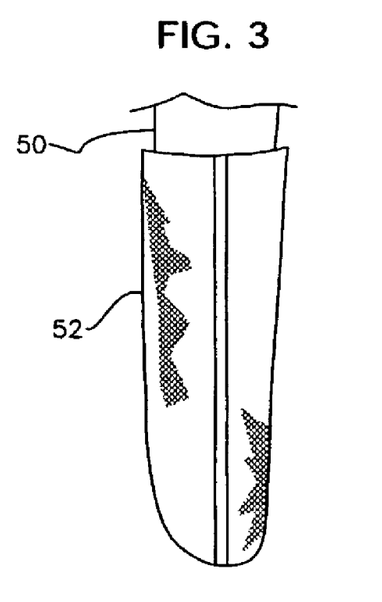
FIG. 3 is a side elevational view of the residual limb covered by the liner.

As indicated in FIG. 2, a prosthetist begins the novel method by placing a prosthetic liner 52 having upper rim 52a onto residual limb 50. FIG. 3 depicts residual limb 50 when fully received within liner 52.

Figure 4:
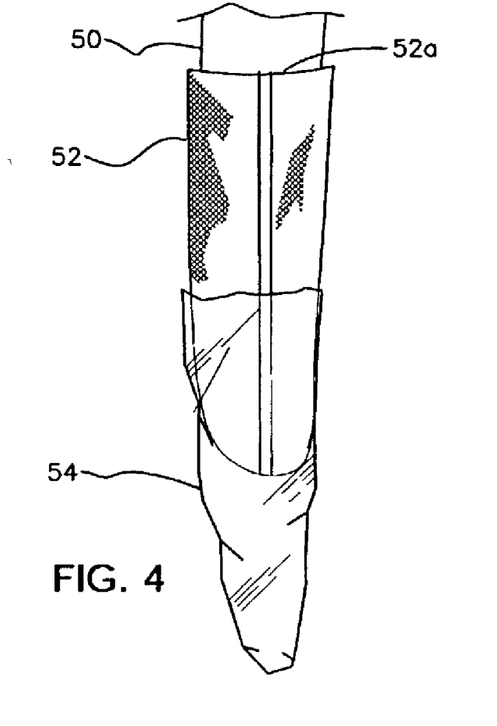
FIG. 4 is a side elevational view depicting a liner being covered by a first plastic separator.

A first plastic separator 54 such as cling wrap is then placed over prosthetic liner 52 as indicated in FIG. 4.

Alternatively, first plastic separator 54 may be applied directly to residual limb 50 in the absence of prosthetic liner 52. Such alternative procedure is not depicted.

Figure 5:
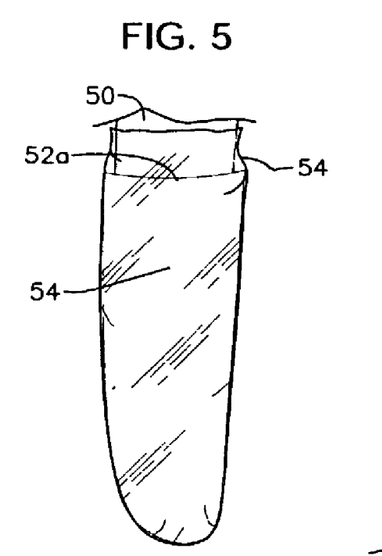
FIG. 5 is a side elevational view depicting the liner fully covered by said first plastic separator.

FIG. 5 depicts liner 52 when first plastic separator 54 has been placed into fully covering relation thereto.

Figure 6:
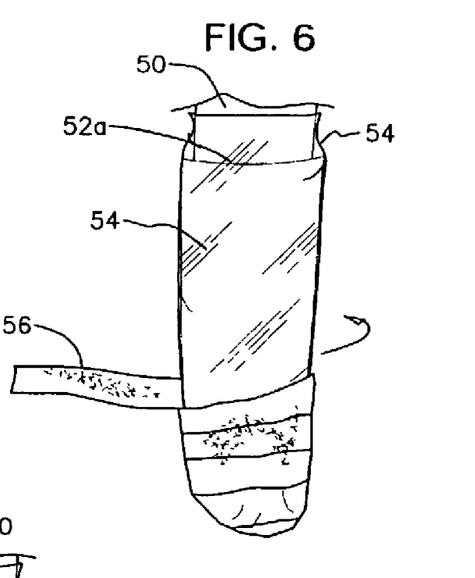
FIG. 6 is a side elevational view depicting the wrapping of the FIG. 5 assembly in plaster bandage means that have been soaked in water.

Plaster bandage means 56 that have been soaked in water are then wrapped around first plastic separator 54 as depicted in FIG. 6.

Figure 7:
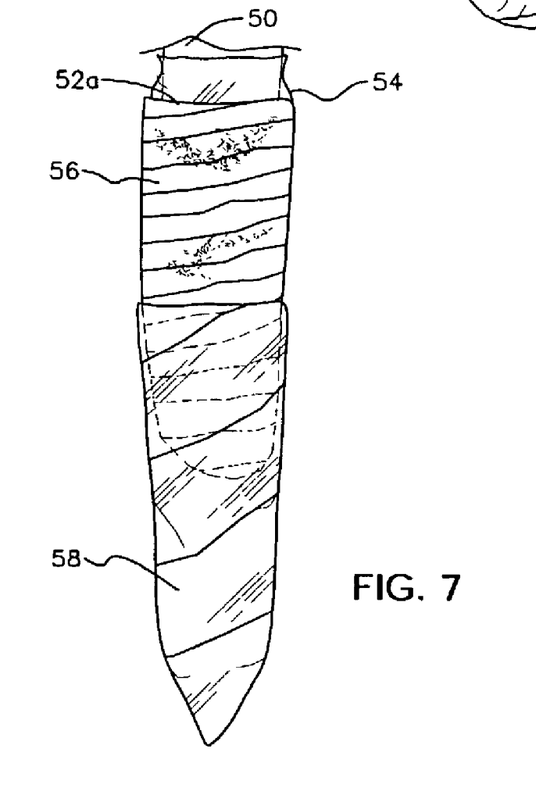
FIG. 7 depicts the assembly of FIG. 6 being covered by a second plastic separator.

Next, as depicted in FIG. 7, plaster bandage means 56 are then covered by a second plastic separator or cling wrap 58.

Figures 8, 9:
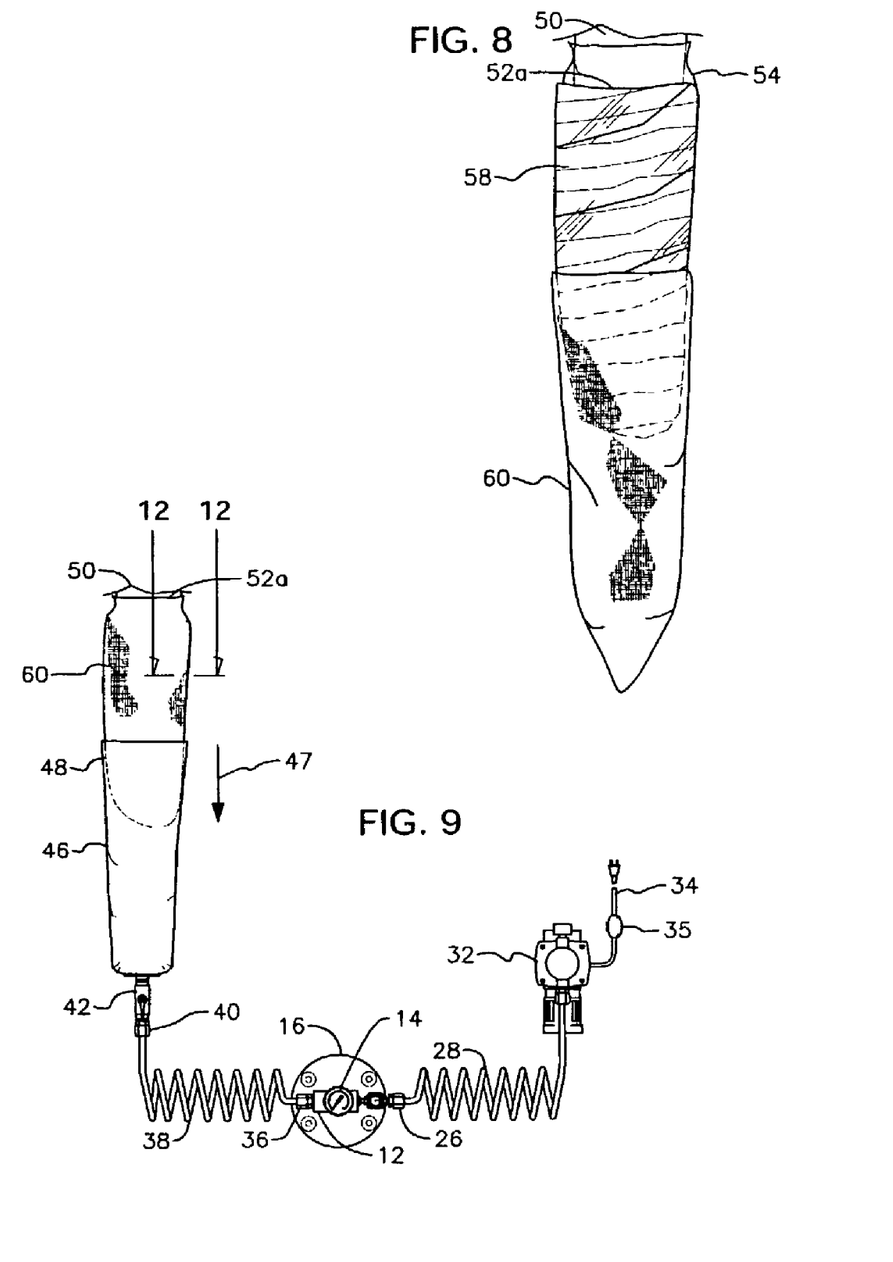
FIG. 8 is a side elevational view depicting the parts of FIG. 7 being covered with a sock or other suitable wick means.
FIG. 9 is a top plan view of the novel apparatus, depicting the parts of FIG. 8 being inserted into a vacuum bladder.

A porous wick means 60, such as a layer of fabric stockinet or a loosely knitted sock as illustrated in FIG. 8, is placed in overlying relation to second plastic separator 58 so that a vacuum can be drawn throughout the length of the residual limb.

The assembly, consisting of residual limb 50, prosthetic liner 52, first plastic separator 54, plaster or urethane bandages 56, second plastic separator 58, and wick 60 are then placed into vacuum bladder 46 as indicated by single-headed directional arrow 47 in FIG. 9.

Figures 10, 11, 12:
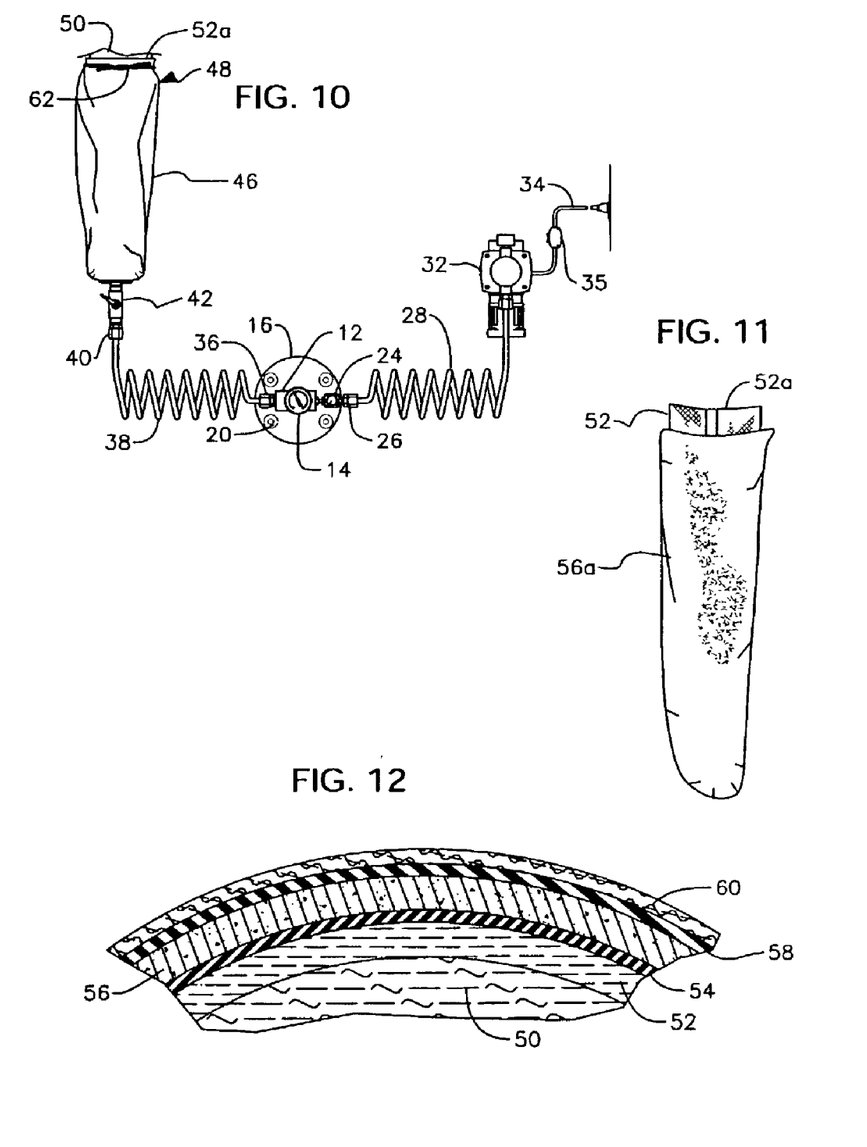
FIG. 10 is a top plan view of the novel assembly when a vacuum is applied to the vacuum bladder.
FIG. 11 is a side elevational view of the positive cast after is it removed from the vacuum bladder.
FIG. 12 is a sectional view taken along line 12—12 in FIG. 9.

FIG. 12, taken along line 12—12 in FIG. 9, depicts the layers of the assembly prior to their introduction into vacuum bladder 46. Depicted are residual limb 50, prosthetic liner 52, first plastic separator 54, plaster means 56, second plastic separator 58, and sock or other suitable wick means 60.

Figure 13:
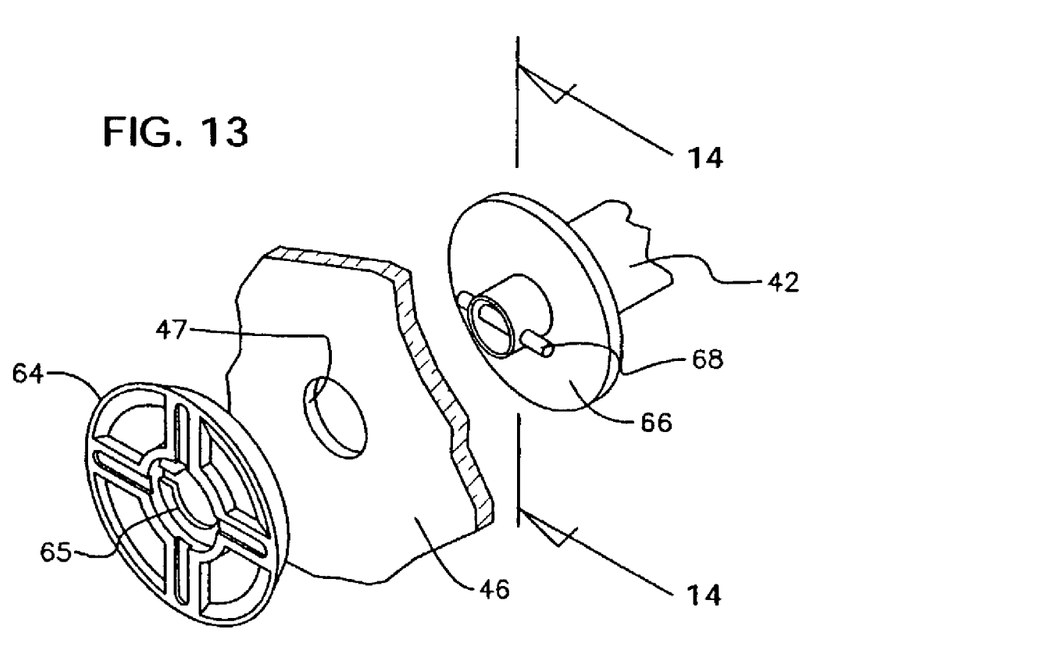
FIG. 13 is an exploded assembly view depicting the parts denoted 13 in FIG. 1.
Figure 14:
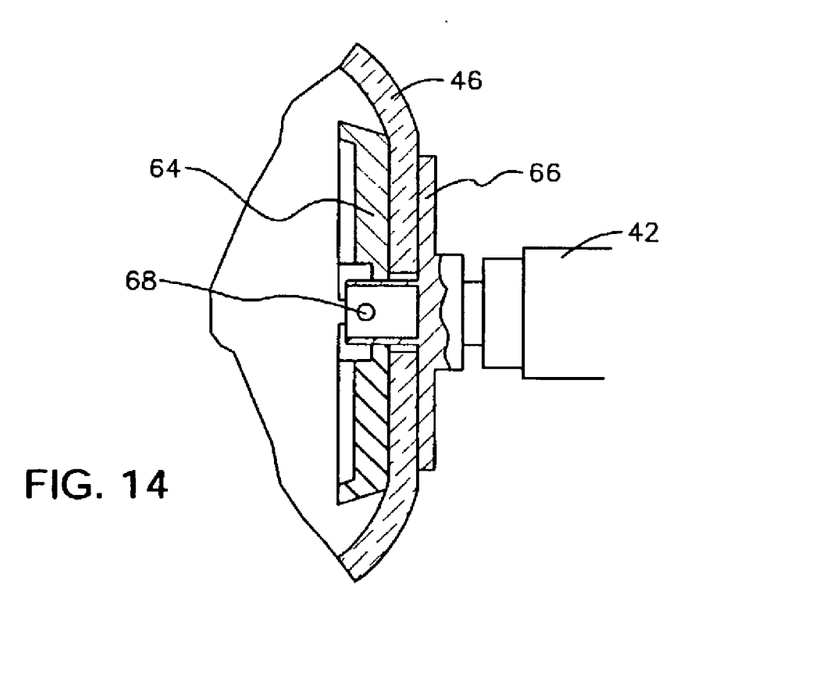
FIG. 14 is a sectional view taken along line 14—14 in FIG. 13.

The manner by which the distal end of vacuum bladder 46 is brought into fluid communication with vacuum means 32 is depicted in FIGS. 13 and 14. The distal end of vacuum bladder 46 is centrally apertured as at 47. Vacuum bladder 46 is positioned in sandwiched relation between locking sleeve 64 and locking plate 66. Locking sleeve 64 includes a plurality of circumferentially spaced apart arms that radiate from a centrally-apertured central hub and terminate in a ring that is concentrically disposed with respect to the hub. Locking plate 66 is centrally apertured and receives the distal end of valve 42 and transversely disposed locking pin 68 extends diametrically through said distal end. A pair of diametrically opposed detents 65 are mounted about the central aperture of the central hub and are spaced apart at their respective opposite ends to enable locking pin 66 to pass therethrough when rotationally aligned therewith. Accordingly, vacuum bladder 46 is rotationally misaligned with said locking pin after said locking pin has extended through the space between the detents, thereby securing the assembly together as depicted in FIG. 14.

After the assembly including residual limb 50 is fully inserted into vacuum bladder 46, a hemostatic latch in the form of rubber tubing 62, depicted in FIG. 10, is tied over proximal end 48 of vacuum bladder 46. The only material in contact with residual limb 50 above rim 52a of liner 52 when said tubing has been tied is first plastic separator 54.

A vacuum is then applied internally to vacuum bladder 46 as depicted in FIG. 10. The prosthetist regulates the amount of vacuum deemed appropriate to the physiology of the residual limb. This vacuum applied internally to vacuum bladder 46 is equivalent to positive pressure applied externally, and causes vacuum bladder 46 to conform tightly to the surface of plaster 56 therebeneath so that the prosthetist can, in effect, see the plaster through the bladder and make manipulations to said plaster means in accordance with his or her professional judgment. Significantly, this is accomplished before plaster means 56 hardens. Accordingly, there is no need to perform the reduction and modification steps on hardened plaster means.

The vacuum is maintained on the residual limb for a predetermined amount of time. Plaster means 56 hardens into a negative cast during such time.

Advantageously, the prosthetist can modify the geometry of plaster means 56 as deemed appropriate for the physiology of the residual limb by manipulating the plaster means through vacuum bladder 46 while plaster means 56 is hardening as aforesaid. Vacuum bladder 46 is sufficiently thin and flexible to conform to the external surface of plaster means 56. After plaster means 56 has hardened, the negative cast is cut longitudinally and removed from the residual limb. Pouring plaster into the negative then produces a positive.

FIG. 11 depicts the negative cast after the plaster means has hardened and the assembly, including residual limb 50, has been removed from vacuum bladder 46, but before said negative cast has been cut and removed from the residual limb. Plaster 56 means is denoted 56a to indicate that it has been manipulated by the prosthetist prior to hardening, i.e., while still covered by vacuum bladder 46.

A properly fitting prosthetic socket is then produced by thermoforming a thermoplastic sheet over the positive cast or by laminating a carbon-epoxy matrix over said positive cast.

The steps of reduction and modification of a hardened positive cast are eliminated because the geometry of the plaster is modified by the prosthetist through the vacuum bladder when the plaster means is hardening. This represents a significant savings in prosthetist time and therefore lowers the cost of the prosthesis. It also lowers the degree of skill required to make the negative cast. Moreover, the final product will accurately reflect the patient's anatomy.

The time consumption and difficulty of working with hard plaster means virtually ensures that the reductions and modifications made on hardened plaster means will be less than optimal. In contrast, the ease of shaping unhardened plaster means beneath vacuum bladder 46 ensures that the modifications will approach or attain perfection, and with much less time consumption and difficulty. The resulting socket will be more comfortable to the user because it will more closely conform to the user's individual physiology.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall there between.

Now that the invention has been described,

What is claimed is:

1. An apparatus for making a prosthetic socket, comprising:
   a vacuum source;
   a vacuum bladder having a closed distal end and an open proximal end;
   a tubing means for providing fluid communication between said vacuum source and said distal end of said vacuum bladder;
   said vacuum bladder adapted to receive a residual limb;
   a first plastic separator disposed in overlying relation to said residual limb;
   a layer of unhardened plaster means disposed in overlying relation to said first plastic separator;
   a wick means disposed in overlying relation to said layer of unhardened plaster means;
   a hemostatic latch for sealing said proximal end of said vacuum bladder when said residual limb, first plastic separator, plaster means, and wick means are positioned within said vacuum bladder;
   whereby a vacuum is capable of being applied internally to said vacuum bladder for an amount of time until said plaster means hardens into a negative cast;
   whereby the residual limb is capable of being manipulated through said vacuum bladder before said plaster means hardens to modify the geometry of the plaster means as appropriate for the physiology of the residual limb; and
   whereby the negative cast is capable of being removed from the residual limb and a the negative cast is capable of having a positive cast formed therein.

2. The apparatus of claim 1, further comprising;
   a thermoplastic sheet that is capable of being thermoformed over the positive cast;
   whereby a prosthetic socket is capable of being made in the absence of reduction and modification of a hard positive cast.

3. The apparatus of claim 1, further comprising;
   a carbon-epoxy matrix that is capable of being laminated over the positive cast;
   whereby a prosthetic socket is capable of being made in the absence of reduction and modification of a hard positive cast.

4. The apparatus of claim 1, further comprising a second plastic separator disposed in overlying relation to said unhardened layer of plaster means.

5. The apparatus of claim 1, further comprising a vacuum regulator disposed between said vacuum source and said vacuum bladder.

6. The apparatus of claim 5, further comprising a valve means disposed between said vacuum regulator and said vacuum bladder.

7. The apparatus of claim 5, further comprising a manifold disposed between said vacuum regulator and said vacuum bladder.

8. The apparatus of claim 7, further comprising a vacuum gauge in fluid communication with said manifold, said vacuum gauge adapted to provide a visual display of pressure within said manifold.

9. An apparatus for making a prosthetic socket, comprising;
- a vacuum source;
- a vacuum bladder having a closed distal end and an open proximal end;
- a tubing means for providing fluid communication between said vacuum source and said distal end of said vacuum bladder;
- said vacuum bladder adapted to receive a residual limb;
- a prosthetic liner disposed in overlying relation to said residual limb;
- a layer of unhardened plaster means disposed in overlying relation to said prosthetic liner;
- a wick means disposed in overlying relation to said layer of unhardened plaster means;
- a hemostatic latch for sealing said proximal end of said vacuum bladder when said residual limb, prosthetic liner, plaster means, and wick means are positioned within said bladder;
- whereby a vacuum is capable of being applied internally to said vacuum bladder for an amount of time until said plaster means hardens into a negative cast;
- whereby the residual limb is capable of being manipulated through said vacuum bladder before said plaster means hardens to modify the geometry of the plaster means as appropriate for the physiology of the residual limb; and
- whereby the negative cast is capable of being removed from the residual limb and the negative cast is capable of having a positive cast formed therein.

10. The apparatus of claim 9, further comprising;
- a thermoplastic sheet that is capable of being thermoformed over the positive cast;
- whereby a prosthetic socket is capable of being made in the absence of reduction and modification of a hard positive cast.

11. The apparatus of claim 9, further comprising;
- a carbon-epoxy matrix that is capable of being laminated over the positive cast;
- whereby a prosthetic socket is capable of being made in the absence of reduction and modification of a hard positive cast.

12. The apparatus of claim 9, further comprising a first plastic separator disposed in overlying relation to said prosthetic liner.

13. The apparatus of claim 12, further comprising a second plastic separator disposed in overlying relation to said unhardened layer of plaster means.

14. The apparatus of claim 9, further comprising a vacuum regulator disposed between said vacuum source and said vacuum bladder.

15. The apparatus of claim 14, further comprising a valve means disposed between said vacuum regulator and said vacuum bladder.

16. The apparatus of claim 14, further comprising a manifold disposed between said vacuum regulator and said vacuum bladder.

17. The apparatus of claim 16, further comprising a vacuum gauge in fluid communication with said manifold, said vacuum gauge adapted to provide a visual display of pressure within said manifold.

* * * * *